United States Patent [19]

Watson, Jr. et al.

[11] 4,332,747

[45] Jun. 1, 1982

[54] PROCESS FOR PRODUCING DIALKYL PHOSPHOROCHLORIDOTHIONATES

[75] Inventors: James W. Watson, Jr., Sandy Hook, Conn.; Michael P. Silvon, Mahopac, N.Y.; Brian J. Lobo, Columbia, Tenn.

[73] Assignee: Stauffer Chemical Company, Westport, Conn.

[21] Appl. No.: 188,153

[22] Filed: Sep. 17, 1980

[51] Int. Cl.³ .............................................. C07F 9/20
[52] U.S. Cl. ...................................................... 260/986
[58] Field of Search .......................................... 260/986

[56] References Cited

U.S. PATENT DOCUMENTS

| | | |
|---|---|---|
| 3,356,774 | 12/1967 | Niermann et al. ................... 260/986 |
| 3,897,523 | 7/1975 | Sorstokke ............................ 260/986 |
| 4,173,603 | 11/1979 | Chen .................................... 260/986 |
| 4,185,053 | 1/1980 | Mirviss et al. ...................... 260/986 |

*Primary Examiner*—Anton H. Sutto
*Attorney, Agent, or Firm*—Vivienne T. White

[57] ABSTRACT

The process of producing a lower alkyl ester of phosphorochloridothioic acid by the chlorination of alkyl esters of dithiophosphoric acid in which the chlorine added after the addition of from 0.63 to 0.86 moles of chlorine per mole of phosphorodithioic acid is diluted with an inert gas. The disclosed process improves product yields, and purity, and advantageously provides for simple HCl recovery.

9 Claims, No Drawings

PROCESS FOR PRODUCING DIALKYL PHOSPHOROCHLORIDOTHIONATES

FIELD OF THE INVENTION

The invention relates to the process for producing phosphorochloridothionates by the chlorination of phosphorodithioic acid.

PRIOR ART

The invention relates to the preparation of esters of phosphorochloridothioic acid. The compounds have the general formula:

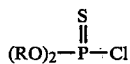

wherein R is a saturated alkyl radical containing between 1 and 8 carbon atoms inclusively. The compounds of this invention are also called O,O-dialkyl-chlorothiophosphonates, or they may be viewed as diesters of chlorothiophosphoric acid chloride. They are characterized by the presence of two ester groups in addition to the acid chloride groups.

A possible reaction route is:

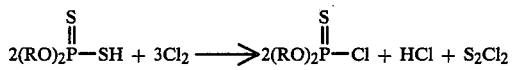

wherein R is a $C_1$–$C_8$ alkyl radical. The above reaction is thought to occur in these two stages:

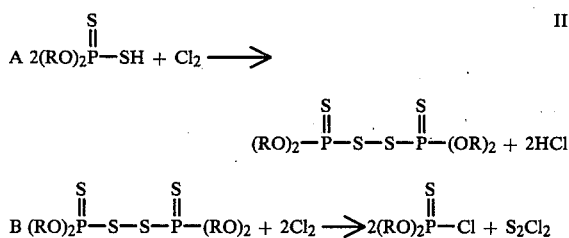

or in these two stages depending on the moles of chlorine reacted with the dithioic acid

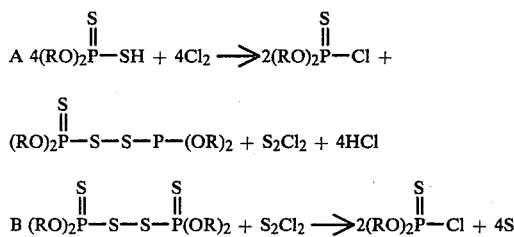

The thionates are valuable intermediates in the manufacture of pesticidal agents, flotation agents, plasticizers, lubricating oil additives, rubber curing compounds, flame retardants and many other useful chemicals.

Various processes for making lower alkyl phosphorochloridothionates by reacting a lower alkyl phosphorodithioic acid with gaseous chlorine have already been described (See U.S. Pat. Nos. 3,897,523; 3,089,890; 2,692,893; 2,482,063; British Pat. No. 646,188; German Pat. No. 1,801,432).

Depending upon the particular process selected for making the dialkyl phosphorochloridothionates, byproducts such as HCl, $S_2Cl_2$ or sulfur or a mixture thereof are invariably obtained. These products which are highly contaminated are technically and commercially difficult to utilize or destroy on an ecologically beneficial condition.

Previous disclosures have indicated that diluting the chlorine in the manufacturing of dialkyl phosphorochloridothionates gives a superior yield of the product. Among the several methods which teach the dilution of the chlorine for producing higher yields of dialkyl phosphorochloridothionates are those disclosed in U.S. Pat. Nos. 4,078,023; 4,173,603; 3,356,744.

U.S. Pat. No. 4,078,023 discloses a process of producing dialkly phosphorochloridothionates by chlorinating the dithioic acid in a two-stage process whereby the chlorine reactant is diluted in both stages.

U.S. Pat. No. 4,173,603 discloses a continuous process for producing dialkyl dithiophosphoric acid and dialkyl phosphorochloridothionates, the latter being produced by reacting the dithioic acid continuously with nitrogen-diluted chlorine. Similarly, U.S. Pat. No. 3,356,744 discloses reacting a $P_2S_5$ suspension with chlorine and an alcohol, wherein the chlorine is diluted with an inert gas such as nitrogen. The prior art cited above, teach diluting all the chlorine added in the reaction process, with the inert gas. The prior art process of diluting all the chlorine reacted with the dithioic acid as described above while resulting in an increased product yield, provides a cumbersome production process, as the diluting gas also dilutes the HCl byproduct making its recovery more difficult.

BRIEF SUMMARY OF THE INVENTION

In accordance with the invention, there is provided a process for manufacturing dialkyl phosphorochloridothionates which overcomes the disadvantage of the prior art process, and advantageously produces a purer product in higher yields.

It has been discovered that when all of the chlorine, added after the addition of an initial 0.63 to 0.86 moles of chlorine per mole of dialkyl phosphorodithioic acid is diluted with an inert gas, in the practice of the invention, superior results are obtained which compares very favorably with the prior art method.

The invention is a process for producing dialkyl phosphorochloridothionates having the formula:

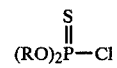

wherein R is an alkyl radical having from 1 to 8 carbon atoms by reacting chlorine gas with a dialkyl phosphorodithioic acid wherein only the chlorine added after the initial from 0.63 to 0.86 moles chlorine per mole of dialkyl phosphorodithioic acid added in the process is diluted with an inert gas.

The novel process is applicable to batch, continuous or semi-continuous processes for manufacturing the dialkyl phosphorochloridothionates.

DETAILED DESCRIPTION OF THE INVENTION

The process of the invention is applicable to a batch process, as for instance, disclosed in U.S. Pat. No. 3,794,703 to Beck et al. (incorporated herein by reference), for producing dialkyl phosphorochloridothionates which comprises reacting dialkyl phosphorodithioic acid with chlorine gas wherein the chlorine added after the addition of from 0.63 to 0.86 moles of chlorine per about a mole of dialkyl phosphorodithioic acid is diluted with an inert gas, in a ratio of about 1:1 to 1:8 preferably in a ratio of inert gas to chlorine of from about 1:1 to 4:1.

The process of the invention additionally is applicable to a continuous process for producing dialkyl phosphorochloridothionates wherein dialkyl phosphorodithioic acid is reacted with the chlorine gas in a two-stage process as described in U.S. Pat. No. 3,897,523 to Sorstokke (incorporated herein by reference). In the process of the invention the chlorine added after the initial addition of from 0.63 to 0.86 moles of chlorine per about a mole of dialkyl phosphorodithioic acid is diluted with an inert gas, preferably in a ratio of inert gas to chlorine of from about 1:1 to 4:1.

The invention also contemplates a semi-continuous process for producing dialkyl phosphorochloridothionates by the reaction of dialkyl phosphorodithioic acid with chlorine gas wherein chlorination is initially accomplished as in the first chlorination stage of the continuous process (U.S. Pat. No. 3,897,523), and thereafter, completing the chlorination in a batch process wherein the chlorine added after the addition of from 0.63 to 0.86 moles of chlorine per about a mole of dialkyl phosphorodithioic acid is diluted with an inert gas, preferably in a ratio of inert gas to chlorine of from about 1:1 to 4:1.

The term "inert gas" as used herein is a gas essentially inert to the reaction of dialkyl dithiophosphoric acid with chlorine. Such gas included but are not limited to the inert gases of the Periodic Table of elements. The inert gas of the disclosed invention is preferably nitrogen due to its highly, non-reactive character wide spread availability and cost. In the practice of the invention as disclosed herein, the inert gas can advantageously be recycled without need to resort to complex recovery means for separating the gas from other byproduct gases such as HCl.

In accordance with the present invention, 0.95 to 1.1 of a dialkyl phosphorodithioic acid is reacted with from 0.90 to 1.5 moles of chlorine gas to form the thionate product. During the process, HCl and other byproducts are evolved as represented in the above equations. The HCl is generally evolved before 0.63 moles of the chlorine has been added to the reaction zone. Advantageously, in accordance with the novel process, the dilution of the chlorine after 0.63 to 0.86 moles of chlorine has been added will not dilute the bulk of the HCl produced, which is therefore easily recoverable. As a result, the vent gases can be diverted from HCl recovery to a simple clean-up device such as an incinerator, during that portion of the process wherein the chlorine is diluted, or the inert gas can be recycled to dilute the chlorine feed to the process.

An additional advantageous feature of the novel process is that it provides a product of increased purity in higher yields. In the process, as the undiluted chlorine reacts with the dithioic acid, some bis(phosphorothioic) sulfide intermediate is produced which also reacts with chlorine or another byproduct $S_2Cl_2$, to produce additional product. As the concentration of the product increases, the chlorine will also react with the product. By diluting the chlorine added toward the end of the reaction, when the concentration of the dialkyl phosphorochloridothionate product approaches its highest level, degradation of the product by the chlorine reaction is substantially prevented. Diluting the chlorine causes it to more selectively react with the disulfide intermediate to form additional product. This results in increased yields and improved chlorine efficiency.

The novel process disclosed herein, as previously indicated is applicable to batch, continuous or semi-continuous production methods. In a batch process, for instance, the dithioic acid is initially reacted with from 0.63 to 0.86 moles of chlorine in a reaction zone, at a temperature of from 10° C. to 80° C. and preferably from 40° C. to 60° C. Thereafter, the remaining chlorine added in the process is diluted with nitrogen, preferably in a 1:1 to 4:1 ratio and added to the mixture. After the chlorine addition is completed the reaction mixture is held for a period of time generally about 1 hour to cause further product to form by the continuous chlorination reaction of the sulfur monochloride byproduct. Thereafter, water is slowly added to the reaction mixture to cause any remaining sulfur monochloride to hydrolyze. The crude product is thereafter obtained by distillation of the reaction mixture.

The batch process described above can also comprise initially chlorinating from 0.8 to 0.91 moles of the dithioic acid reactant in a reaction zone with the initial from 0.63 to 0.83 moles of chlorine added in the process and thereafter, charging the remaining 0.15 to 0.3 moles of the dithioic acid to the reactor with the remaining 0.04 to 0.87 moles of the chlorine diluted with nitrogen. On completion of the chlorine addition, the process continues as in the batch process disclosed above.

A continuous process utilizing the novel method disclosed herein, comprises the steps of continuously introducing the dialkyl phosphorodithioic acid and chlorine into a first reaction mixture containing a dialkyl phosphorochloridothionate maintained at a temperature of from about 40°–80° C. in a first chlorination zone wherein dialkyl phosphorothioic acid and chlorine are reacted. The amount of chlorine introduced into the first chlorination zone should be from about 0.63 to 0.86 moles of chlorine. The reaction mixture of the first chlorination zone is then continuously transferred to a second chlorination zone wherein said first reaction mixture is continuously reacted with chlorine diluted with an inert gas in a second reaction mixture, maintained at a temperature from 20° C. to 80° C. with the lower temperatures preferred to inhibit the formation of the $S_2Cl_2$ byproduct. The amount of chlorine introduced into the second chlorination zone should be sufficient to bring the total amount of chlorine introduced into said first and second chlorination zones to between about 0.90 to about 1.5 moles of chlorine per 0.95–1.1 mole of dialkyl phosphorothioic acid. Only the added chlorine after the initial from 0.63 to 0.86 moles of chlorine added in the practice of the invention is diluted with an inert gas which is the continuous process as disclosed above should be added in the second chlorination zone.

As disclosed in U.S. Pat. No. 3,897,523 the reaction mixture containing the thionate product with impurities is passed to a continuous film evaporation zone where a vaporous fraction comprising the thionate is separated from the mixture and then passed to a condenser where the bulk portion of the vapor is condensed to a liquid containing the thionate and impurities. The crude or impure condensate is then passed to a purification zone to remove the impurities. The purified thionate in solution is then dried and the final product recovered.

The following examples are described in detail below for the purpose of better illustrating the invention.

EXAMPLE 1

Dimethyl phosphorochloridothionate (DMPCT) was produced in a reactor, in a batch process by chlorinating 166.3 grams of dimethyl phosphorodithioic acid (DMPTA) with 71 grams of chlorine. The chlorine was delivered over a 1 hour period at a reaction temperature of 55° C. After about 0.85 moles of the chlorine was delivered (~60 grams), nitrogen was added to dilute the remaining chlorine and both were charged to the reactor at a rate of 0.0198 m.$^3$/hr. (0.75 ft.$^3$/hr.). The reactants were then held in the reactor for 1 hour at 60° C. Thereafter, water was slowly added over a half hour period, and the mixture containing the product was then distilled at 80° C. (with a vapor temperature of 43° C.) under 1 mm. of mercury. The DMPCT distillate product obtained weighed 142.7 gms. corresponding to a yield of crude DMPCT of 87.5% based on the weight of the DMPTA used. The assay obtained by gas chromatography (G.C.) was 97.5%.

EXAMPLES 2, 3, 4 and 5

The method used in Example I was repeated using the same weights and reactants. Nitrogen, however, was delivered at a rate of 0.0793 m.$^3$/hr. (2.8 ft.$^3$/hr.) to dilute the final 11 grams of chlorine, corresponding to a 4:1 ratio. The results obtained were:

| Example | Crude Yield DMPCT (based on weight of DMPTA) | Assay of Crude (% by G.C.) |
| --- | --- | --- |
| 2 | 79.6 | 97.2 |
| 3 | 87.6 | 94.3 |
| 4 | 79.6 | 97.1 |
| 5 | 90.5 | 96.0 |

CONTROL 1 and 2

DMPCT was produced in two control batch process runs. The process used was that disclosed in Examples 1–5 using the same reactants in the amounts specified. In the controls, however, the added chlorine was not diluted. The results obtained were as follows:

| | DMPCT | |
| --- | --- | --- |
| | Crude Yield (% based on wt. of DMPTA) | Assay of Crude by G.C. % |
| Control 1 | 78.8 | 89.4 |
| Control 2 | 77.6 | 87.9 |

EXAMPLE 6

DMPCT was produced in a batch reactor as in the prior examples by initially chlorinating 150.3 grams of DMPTA (representing 90% of the total DMPCT reacted in the process) with 60 grams of chlorine (0.85 moles).

An additional 16.0 grams of DMPTA was "dribbled" into the reactor while nitrogen and chlorine were delivered in a 4:1 N$_2$:Cl$_2$ ratio. The total chlorination was accomplished over a period of 1 hour at a reaction temperature of 55° C. The reaction mixture was then held for 1 hour at 60° C. prior to adding water. The mixture was distilled at a temperature of 80° C. (vapor temperature of 42° C.) under a vacuum of 0.3 mm. of Hg. The DMPCT distillate product obtained weighed 134.1 gms. corresponding to a yield of crude DMPCT of 81.9% based on the weight of DMPTA used with a purity of 97.9%.

EXAMPLE 7

Diethyl phosphorochloridothionate (DEPCT) was produced by chlorination of 196 gms. diethyl phosphorodithioic acid (DEPTA) in a batch reactor using 60 grams of chlorine (0.85 moles). An additional 11 grams of chlorine diluted with nitrogen in a 1:4 ratio, was then charged to the reactor. The nitrogen was fed to the chlorine line at a rate of about 0.0793 m.$^3$/hr. (2.8 std. ft$^3$/hr.). The total chlorine addition was accomplished over a period of 1 hour at a reaction temperature of 55° C.

After chlorination, the reactants were held for 1 hour at 60° C. Thereafter, water was added, and the reaction mixture was distilled at 87° C. (vapor temperature 60° C.) under a vacuum of 0.5 mm. Hg. The DEPCT distillate product obtained weighed 161.8 grams corresponding to a crude yield of 83.9% based on the weight of the DEPTA used with a purity of 99.2%.

EXAMPLE 8

DEPCT was prepared in a reactor by chlorinating 196 grams of DEPTA with 59.2 grams of chlorine (85% of total). Another 11.8 gms. of chlorine diluted with nitrogen in a 1:4 ratio was delivered to the reactor in a 1:4 ratio. The entire chlorine addition was accomplished over a 1 hour period at 55° C. After chlorination the reactants were held for 1 hour at 60° C. Water was then added and the reaction mixture was distilled at a temperature of 86° C. under 0.5 mm. Hg. The DEPCT distillate product obtained weighed 165.4 gms. which corresponded to a 84.4% yield, based on the weight of DEPTA used, having a purity of 99.6%.

EXAMPLE 9

Using the method of Example 8, 196 gms. of DEPTA was initially chlorinated with 60 gms. of chlorine. The remaining 11 gms. (0.15 moles) of chlorine was diluted with nitrogen in a 1:4 ratio. After chlorination was completed the chlorine delivery lines were flushed with nitrogen to insure total chlorine delivery which amounted to a 97.5% chlorination. The DEPCT distillate obtained weighed 168.6 gms. corresponding to a crude DEPCT yield of 87.3% based on the weight of DEPTA used with a purity of 99.4%.

CONTROL 3 and 4

Control DEPCT production runs were made using the process disclosed in Examples 7–9, and amounts of the reactants specified therein, except that none of the chlorine added was diluted. The results were as follows:

| | DEPCT | |
| --- | --- | --- |
| Control | Crude Yield (% based on weight of DEPTA) | Assay of Crude % by G.C. |
| 3 | 84.5 | 98.9 |
| 4 | 78.2 | 98.0 |

What is claimed is:

1. An improved process for producing dialkyl phosphorochloridothionates having the formula:

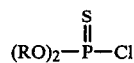

where R is a lower alkyl having from 1 to 8 carbon atoms, by the reaction of dialkyl phosphorodithioic acid with chlorine gas, wherein the chlorine added after the initial from 0.63 to 0.86 moles of chlorine per mole of dialkyl phosphorodithioic acid added in the process is diluted with an inert gas.

2. The process of claim 1, wherein the dialkyl phosphorodithioic acid is reacted with chlorine in a ratio of from 0.95 to 1.5 moles of chlorine per 0.95–1.1 mole of dithioic acid.

3. An improved process for producing dialkyl phosphorochloridothionates having the formula:

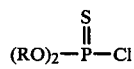

where R is a lower alkyl having from 1 to 8 carbon atoms, comprising the steps of (a) reacting from 0.95 to 1.1 moles of a corresponding dialkyl phosphorodithioic acid with from 0.63 to 0.86 moles of chlorine in a reaction zone to form a reaction mixture; (b) adding to the reaction mixture of the reaction zone a further 0.04 to 0.87 moles of chlorine diluted with nitrogen; (c) holding the above reactants in the reaction zone for a period of time to allow further product formation; (d) adding water to the reaction mixture; and (e) distilling the water-treated reaction mixture to recover the dialkyl phosphorochloridothionate.

4. An improved process of producing dialkyl phosphorochloridothionates having the formula:

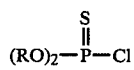

wherein R is a lower alkyl having from 1 to 8 carbon atoms, comprising the steps of (a) reacting 0.80 to 0.91 moles of a corresponding dialkyl phosphorodithioic acid with from 0.63 to 0.83 moles of chlorine in a reaction zone to form a reaction mixture; (b) adding simultaneously to the reaction mixture of the reaction zone a further 0.5 to 0.3 moles of the dithioic acid and from 0.04 to 0.87 moles of chlorine diluted with nitrogen; (c) holding the reactants in the reaction zone a period of time to allow for increased product formation; (d) thereafter adding water to the reaction mixture; and (e) distilling the water-treated reaction mixture to recover the dialkyl phosphorochloridothionate.

5. An improved process of continuously producing dialkyl phosphorochloridothionates having the formula:

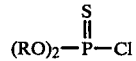

wherein R is a lower alkyl having from 1 to 8 carbon atoms, comprising the steps of (a) continuously introducing dialkyl phosphorodithioic acid and chlorine into a first reaction mixture containing a dialkyl phosphorochloridothionate maintained at a temperature of from about 40° C.–80° C. in a first chlorination zone wherein dialkyl phosphorodithioic acid and chlorine are reacted, the amount of chlorine introduced into said first chlorination zone is between 0.63 to 0.86 moles of chlorine per 0.95 to 1.1 moles of the dithioic acid; (b) continuously transferring a portion of the first reaction mixture to a second chlorination zone wherein said first reaction mixture is continuously reacted with chlorine diluted with an inert gas in a second reaction mixture maintained at a temperature of from 20° C. to 80° C., the amount of chlorine introduced into said second chlorination zone is sufficient to bring the total amount of chlorine introduced into said first and second chlorination zone to between 0.90 and about 1.5 moles of chlorine per 0.95 to 1.1 moles of dialkyl phosphorodithioic acid; and (c) recovering the dialkyl phosphorochloridothionate product.

6. The process of claim 1, 3, 4 or 5, wherein the inert gas used to dilute the chlorine is nitrogen.

7. The process of claim 1, 3, 4 or 5, wherein the diluted chlorine is comprised of inert gas and chlorine in a ratio of from 1:1 to 4:1.

8. The improved process of claim 1, 3, 4 or 5, wherein the dialkyl phosphorodithioic acid used in the process is dimethyl phosphorodithioic acid.

9. The improved process of claim 1, 3, 4 or 5, wherein the dithioic acid used in the process is diethyl phosphorodithioic acid.

* * * * *